United States Patent [19]
Bybee et al.

[11] Patent Number: 5,467,379
[45] Date of Patent: Nov. 14, 1995

[54] APPARATUS FOR TAKING X-RAYS OF AN AIR BAG INFLATOR DURING A FIRING CYCLE

[75] Inventors: Steven D. Bybee, Roy; A. Kim Cummings, Hooper, both of Utah

[73] Assignee: Morton International, Inc., Chicago, Ill.

[21] Appl. No.: 343,623

[22] Filed: Nov. 22, 1994

[51] Int. Cl.$^6$ .................................................... G01N 23/04
[52] U.S. Cl. ................... 378/57; 378/58; 378/208
[58] Field of Search ...................... 340/436, 438; 378/62, 57, 210, 58, 68, 87, 204, 208, 209; 280/741, 743.1

[56] References Cited

U.S. PATENT DOCUMENTS

| | | | |
|---|---|---|---|
| 4,092,537 | 5/1978 | Stewart | 378/58 |
| 5,065,418 | 11/1991 | Bermbach et al. | 378/57 |
| 5,347,561 | 9/1994 | Ebinuma | 378/204 |

*Primary Examiner*—David P. Porta
*Assistant Examiner*—Don Wong
*Attorney, Agent, or Firm*—Philip C. Peterson; Gerald K. White

[57] ABSTRACT

Apparatus for x-ray viewing of the firing cycle of an air bag inflator includes a pressure tank for containing an inflator during a firing cycle thereof having an access opening in a wall for receiving the inflator. A mounting ring is secured in place in the access opening having a stop flange at an inner open end for engaging the base of the inflator when inserted into the open end of the housing and limiting the amount of insertion of the inflator into the tank. A pressure plug is removably securable in the mounting ring to engage the base of the inflator for rigidly securing the same in a fixed position in the tank and sealing off the tank during a firing cycle. An x-ray apparatus and film pack or recorder are disposed on opposite sides of the tank to view the progress of the ignition process during a firing cycle of the inflator. A control system is interconnected between the x-ray apparatus and the inflator to initiate a firing cycle and take a number of x-ray photos in sequence as the ignition process takes place.

20 Claims, 2 Drawing Sheets

APPARATUS FOR TAKING X-RAYS OF AN AIR BAG INFLATOR DURING A FIRING CYCLE

BACKGROUND OF THE INVENTION

1. Field of the Invention

The present invention relates to a new and improved test apparatus for taking x-rays of an air bag inflator during a firing cycle and more particularly to a new and improved pressure tank assembly for securely holding an air bag inflator in a fixed position permitting an unobstructed x-ray view of the inflator along a central axis of an ignition train in the body of the inflator.

2. Background of the Prior Art

Heretofore when testing air bag inflators in a pressure tank it has been difficult to obtain high quality unobstructed x-rays of the inflator ignition train during a firing cycle.

Moreover, because a high gas pressure of up to 3000 psi is generated in a very short time when a firing cycle is initiated it has been difficult to rigidly secure the inflator in a fixed position in a test tank without gas leakage.

OBJECTS OF THE INVENTION

It is an object of the present invention to provide a new and improved apparatus for taking x-rays of an air bag inflator during a firing cycle thereof.

Another object of the present invention is to provide a new and improved pressure tank apparatus in which an air bag inflator can be secured against movement during a firing cycle while affording a clear and unobstructed x-ray view of the operation of the ignition train of the inflator.

Yet another object of the present invention is to provide a new and improved pressure tank apparatus which is easy to use, easy to load and unload with an air bag inflator, reliable in operation without leakage and capable of providing high quality x-ray images during the firing cycle of an air bag inflator.

Another object of the present invention is to provide a new and improved pressure tank and x-ray apparatus which is capable of clearly disclosing on x-ray film the sequential movement of an ignition pulse or flash initiated to ignite gas generating material of the inflator during a firing cycle.

BRIEF SUMMARY OF THE PRESENT INVENTION

The foregoing and other objects and advantages of the present invention are accomplished in a new and improved apparatus for x-ray viewing of the firing cycle of an air bag inflator including a pressure tank for containing an air bag inflator during a firing cycle thereof. The tank has an access opening in a wall thereof for receiving the inflator and a mounting ring is secured in place in the access opening having a stop flange at an inner open end for engaging a base of the inflator when the inflator is inserted into the open end of the housing. The stop flange supports and positions the inflator and limits the amount of insertion of the inflator into the tank. A pressure plug is removably securable in the mounting ring to engage the base of the inflator and rigidly hold the inflator in a fixed position in the tank while effecting a seal of the access opening. An x-ray apparatus and film pack or recorder are disposed on opposite sides of the tank to view the progress of the ignition process during a firing cycle of the inflator. A control system is interconnected between the x-ray apparatus and the inflator to initiate a firing cycle and take a sequence of x-ray pictures of the ignition process.

BRIEF DESCRIPTION OF THE DRAWINGS

For a better understanding of the present invention, reference should be had to the following detailed description taken in conjunction with the drawings, in which.

DETAILED DESCRIPTION OF A PREFERRED EMBODIMENT OF THE INVENTION

Figure 3:
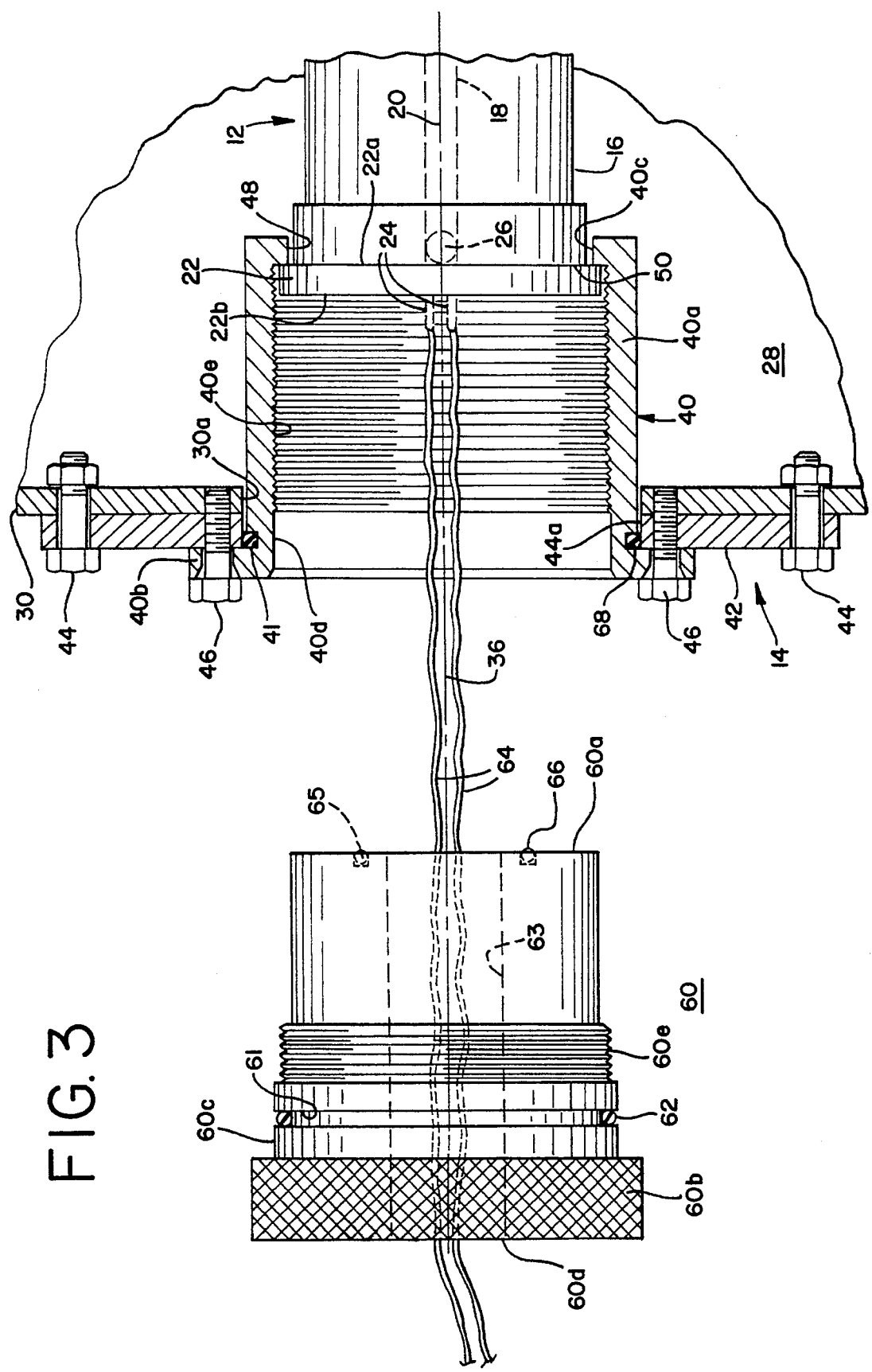
FIG. 3 is an enlarged cross-sectional view taken substantially along lines 3—3 of FIG. 2.

Referring now more particularly to the drawing, therein is illustrated a new and improved apparatus 10 for x-ray viewing of an air bag inflator 12 during a firing cycle thereof while contained in a pressure tank 14. The air bag inflator 12 may be a type shown and described in copending U.S. patent application Ser. No. 08/114,211, filed Aug. 30, 1993, and incorporated herein by reference. The inflator 12 includes an elongated cylindrical body 16 having a central ignition core 18 running between opposite ends of the body along a central longitudinal axis 20. At one end the inflator 12 is provided with an enlarged base 22 having a pair of protruding electrical terminals 24 adjacent a central portion thereof electrically connected to an ignition squib 26 (FIG. 3) at the base end of the ignition train 18.

In accordance with the features of the present invention, the pressure tank 14 includes a cylindrically-shaped, tubular side wall 28 extending between a circular front end wall 30 and a rear end wall 32. The tank 14 may be provided with support legs 34 to elevate a horizontal centerline 36 thereof to a convenient working level. The front end wall 30 is formed with a circular access opening 30a somewhat larger in diameter than the base 22 of the air bag inflator 12 and a generally cylindrical-shaped mounting ring 40 is seated in the access opening extending inwardly into the interior of the pressure tank 14.

The front end wall 30 is provided with an annular stiffening ring 42 around the access opening 30a which is bolted in place with a plurality of bolts and nuts 44. The stiffening ring 42 has a central opening 42a large enough to accommodate a central body portion 40a of the mounting ring 40. At the outer end, the mounting ring 40 is formed with a radially outwardly extending flange 40b which is secured to the front end wall 30 and the stiffening ring 42 by a plurality of cap screws 46.

At the open inner end the mounting ring 40 is formed with a radially inwardly directed stop flange 40c having a central opening 48 with a diameter less than that of the base 22 of the air bag inflator 12. The stop flange 40c provides a radial, annular stop surface 50 which is engaged by a shoulder surface 22a of the base 22 of the air bag inflator 12 upon insertion of the inflator into the mounting ring 40. This engagement limits the amount of insertion of the inflator 12 into the pressure tank 14 and precisely positions the inflator with respect to the tank for unobstructed x-ray viewing along the length of the inflator central axis 20 as shown in the drawing.

In order to firmly secure the air bag inflator 12 in the tank 14 during a firing cycle, a pressure plug 60 is provided having an annular inner end face 60a adapted to bear against an outer end face 22b of the base 22 of the inflator. At an outer end portion, the plug 60 is provided with a knurled segment 60b to facilitate hand tightening and loosening of the plug in the mounting ring 40. Adjacent the knurled segment 60b, the plug 60 is formed with a smooth cylindrical segment 60c dimensioned to closely interfit with an outer bore segment 40d of the mounting ring 40 when the plug is fully inserted.

The smooth segment 60c of the plug 60 is formed with a groove 61 and an "O" ring seal 62 is mounted in the groove to tightly seal between the segments 60c and 40d respectively when the plug is fully inserted in the mounting ring. A central bore or passage 63 extends between the inner end face 60a and an outer end face 60d of the plug 60 in order to accommodate electrical leads 64 connected to the terminals 24 on the base 22 of the inflator. The inner end face 60a of the plug 60 is formed with an annular groove 65 around the passage or bore 63 and an "O" ring seal 66 is mounted in the groove to seal between the end face 22b of the inflator 12 and the inner end face 60 of the plug. The mounting ring 40 is formed with a threaded bore 40e extending between the smooth wall segment 40d adjacent the outer end and the stop surface 50 of the flange 40c at the inner end of the ring. The plug 60 is formed with external threads 60e for threaded engagement in the bore 40e to firmly hold the plug in place in the mounting ring 40 with the base 22 of the inflator 12 captured between the stop surface 50 of the stop flange 40c and the inner end face 60a of the plug.

In order to further ensure a tight seal between the mounting ring 40 and the stiffening ring 42, a groove 41 is formed in outer surface of the mounting ring adjacent the outer end flange 40b and an "O" ring seal 68 is mounted in the groove to effect a tight pressure seal between the rings.

It is thus seen that the plug 60 is easily threaded into place by hand in the mounting ring 40 after the air bag inflator 12 to be tested and x-rayed is seated with the base 22 thereof pressed against the stop surface 50 by the inner end face 60a of the plug. The air bag inflator 12 is securely held in this precise position while a firing cycle is taking place and thereafter the plug 60 is readily unthreaded from the mounting ring 40 so that the inflator 12 may be withdrawn for inspection and/or further testing. The pressure tank 14 is tightly sealed by the plug 60 and the "O" rings 62, 66 and 68 so that the gas pressure achieved during the firing cycle of the inflator 12 can be precisely measured on a time basis.

Figure 1:
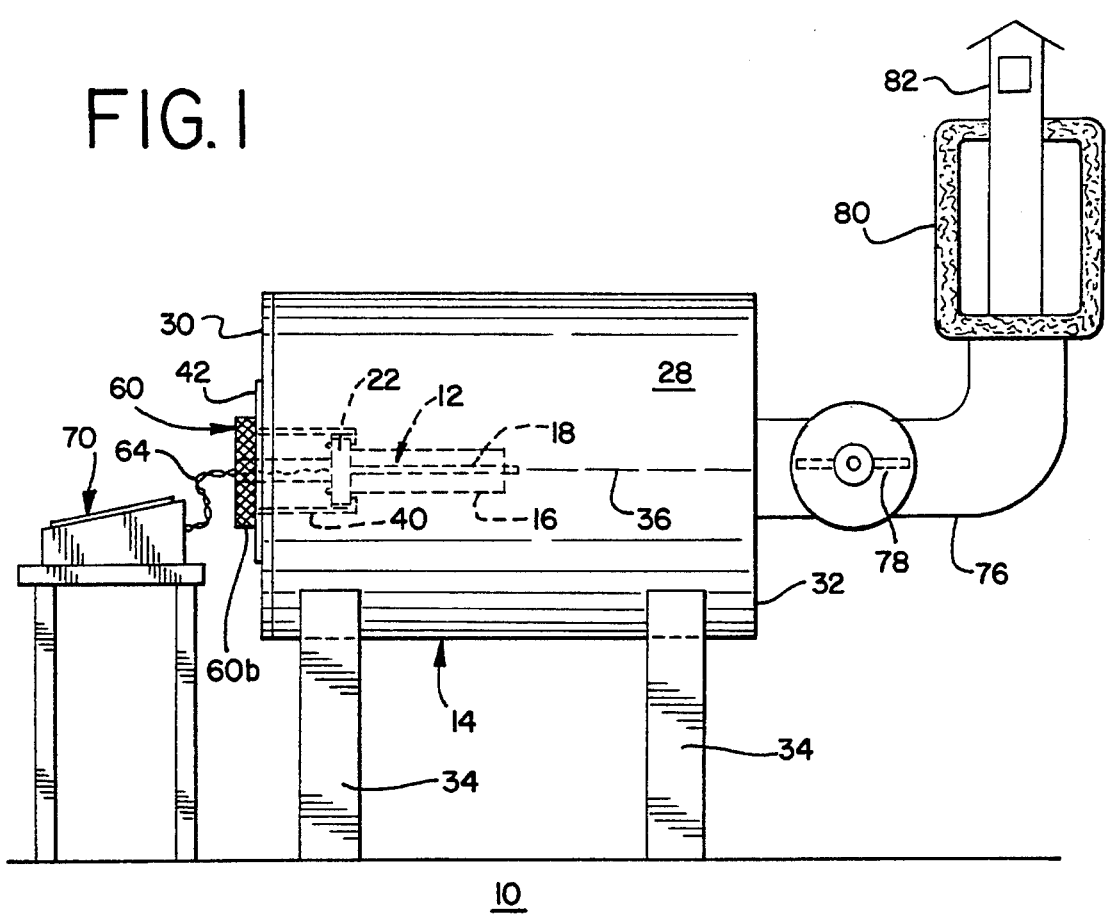
FIG. 1 is a side elevational view of a new and improved apparatus for taking x-rays of an air bag inflator during a firing cycle constructed in accordance with the features of the present invention.
Figure 2:
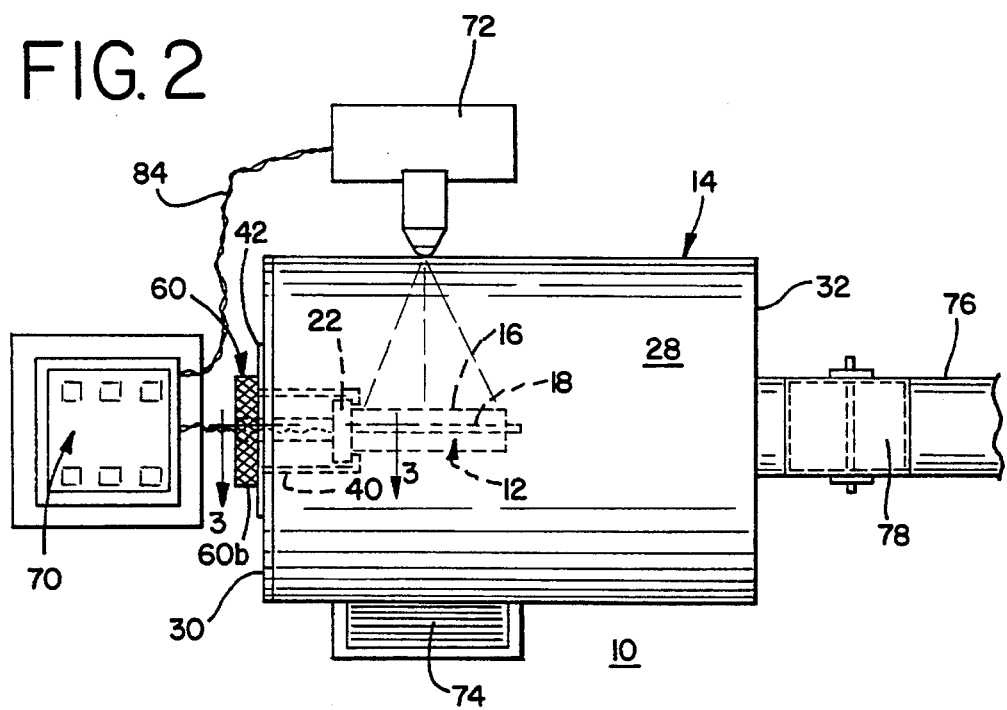
FIG. 2 is a top plan view of the apparatus.

In accordance with the present invention, after an air bag inflator 12 is positioned in the pressure tank 14 as described with electrical leads 64 connected to the terminals 24 of the ignition squib 26, actuation of a firing cycle can be commenced. A control panel 70 is provided to send a firing pulse through the leads 64 to the inflator 12 and to initiate a series of x-ray photos by means of an x-ray apparatus 72 positioned on one side of the pressure tank 14 to generate a series of x-ray emissions in timed sequence to capture the travel of the ignition flash through the core 18 of the inflator moving from the squib 26 along the axis 20 to the opposite end of the inflator. As shown in FIGS. 1 and 2, because the mounting ring 14 supports the inflator 12 with its base 22 positioned well inside of the front wall 30 of the pressure tank 14, a clear and unobstructed x-ray view of the entire length of the ignition train or core 18 of the inflator is afforded to the x-ray apparatus 72 positioned to direct x-ray energy generally transversely to the longitudinal axis 36 of the tank and the coincident center axis 20 of the inflator.

A film pack or recording apparatus 74 is positioned on an opposite side of the pressure tank 14 to receive the x-ray images of the ignition pulse or flash traveling from the base 22 of the inflator 12 to the opposite end. Preferably, a series of x-ray photos are taken in timed sequence to depict the travel of the ignition pulse in a firing cycle.

After a firing sequence has been completed for an inflator 12, the hot combustion products generated in the pressure tank 14 are exhausted by means of an exhaust duct pipe 76 connected to an opening in the rear wall 32 of the pressure tank. An exhaust valve 78 is provided in the exhaust duct 76 and a filter 80 is provided for entrapping contaminants from the generated gases before discharge to the atmosphere via an exhaust stack 82. The control panel 70 is interconnected to the x-ray apparatus 72 via a multi-conductor control cable 84 and the timing of the x-ray photos and the initiation of a firing cycle are precisely synchronized.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. Apparatus for x-ray viewing of an air bag inflator, during a firing cycle comprising:

pressure tank means for holding said inflator during a firing cycle thereof having an access opening in a wall for receiving said inflator;

pressure plug housing means mounted in said access opening having stop means at an inner open end for engaging a base at an end of said inflator inserted into said open end for limiting the amount of insertion of said inflator into said tank means; and pressure plug means removably securable in said housing means engageable with said base of said inflator for rigidly securing the same in fixed position in said tank means and sealing said housing means.

2. The apparatus of claim 1, wherein:

said pressure plug means and said housing means are threadably engageable.

3. The apparatus of claim 1, including:

resilient seal means between said housing means and said wall around said access opening.

4. The apparatus of claim 1, including:

resilient seal means on said pressure plug means for sealing engagement with said base of said air bag inflator in said tank means.

5. The apparatus of claim 1, wherein:

said pressure plug means is formed with a passage between opposite ends for accommodating an electrical wire used for initiating said firing cycle of said air bag inflator.

6. The apparatus of claim 5, including:

resilient seal means on an inner one of said opposite ends of said pressure plug means for sealing engagement between said inner end and said base of said inflator around said passage.

7. The apparatus of claim 1, wherein:

said housing means includes a threaded bore for receiving said pressure plug means; and said stop means includes an annular flange extended radially inwardly of said bore at said inner open end for engaging said base of said air bag inflator.

8. The apparatus of claim 7, wherein:

said pressure plug means includes an externally threaded body for threaded engagement in said bore, and an inner end facing said base of said air bag inflator for holding the same against said flange of said housing means.

9. The apparatus of claim 1, wherein:

said pressure tank means has a side wall joining said wall around said access opening; and including:

x-ray means on opposite sides of said side wall aligned with said air bag inflator in said pressure tank.

10. The apparatus of claim 9, including:

control means for initiating a firing cycle of said air bag inflator in said pressure tank and controlling said x-ray means.

11. A testing system for x-ray viewing of the firing cycle of an air bag inflator having a base at one end and an ignition train extending longitudinally from the base along the center of the body of the inflator, comprising:

a pressure containment tank for securely positioning said inflator during a firing cycle thereof having an access opening in a wall for receiving said inflator;

a mounting ring secured to said wall around said access opening having a stop flange at an inner open end for engaging said base of said inflator when inserted into said open end for limiting the amount of insertion of said inflator into said tank; and a pressure plug threadedly engageable in said ring and engageable with said base of said inflator for rigidly securing said inflator in fixed position in said tank and sealing off said mounting ring.

12. The system of claim 11, including:

a resilient seal between said mounting ring and said wall of said tank around said access opening.

13. The system of claim 11, including:

a resilient seal mounted on said pressure plug for sealing engagement with said base of said air bag inflator while mounted in said tank.

14. The system of claim 11, wherein:

said pressure plug includes a central passage extending between opposite ends for accommodating an electrical wire connected to said inflator for initiating said firing cycle.

15. The system of claim 14, including:

a resilient seal mounted on an inner end of said pressure plug for sealing engagement with said base of said inflator around said passage.

16. The system of claim 11, wherein:

said mounting ring includes a threaded bore for receiving said pressure plug and said stop flange extends radially inwardly of said bore at said inner open end for engaging said base of said air bag inflator.

17. The system of claim 16, wherein:

said pressure plug includes an externally threaded body for threaded engagement in said bore of said mounting ring, and an inner end facing said base of said air bag inflator for holding the same against said stop flange of said mounting ring.

18. The system of claim 11, wherein:

said pressure tank has a tubular side wall joining said first mentioned wall around said access opening spaced outwardly and concentric of said mounting ring.

19. The system of claim 18, including:

x-ray means on opposite sides of said tubular side wall aligned on opposite sides of said air bag inflator mounted in said pressure tank.

20. The apparatus of claim 19, including:

control means for initiating a firing cycle of said air bag inflator mounted in said pressure tank and for controlling said x-ray means to x-rays of said ignition train during said firing cycle.

\* \* \* \* \*